(12) United States Patent
Nuñez et al.

(10) Patent No.: US 11,702,500 B2
(45) Date of Patent: Jul. 18, 2023

(54) BIOMEDICAL DEVICES

(71) Applicant: Bausch + Lomb Ireland Limited, Dublin (IE)

(72) Inventors: Ivan M. Nuñez, Bluffton, SC (US); Lynn Coullard, Williamson, NY (US); Katie L. Poetz, Scottsdale, AZ (US)

(73) Assignee: Bausch + Lomb Ireland Limited, Dublin (IE)

( * ) Notice: Subject to any disclaimer, the term of this patent is extended or adjusted under 35 U.S.C. 154(b) by 0 days.

(21) Appl. No.: 17/694,981

(22) Filed: Mar. 15, 2022

(65) Prior Publication Data

US 2022/0298287 A1   Sep. 22, 2022

Related U.S. Application Data

(60) Provisional application No. 63/161,002, filed on Mar. 15, 2021.

(51) Int. Cl.
| | | |
|---|---|---|
| *C08G 18/12* | (2006.01) | |
| *C08G 18/32* | (2006.01) | |
| *C08G 18/61* | (2006.01) | |
| *C08G 18/64* | (2006.01) | |
| *G02B 1/04* | (2006.01) | |
| *A61L 27/18* | (2006.01) | |
| *A61L 29/06* | (2006.01) | |
| *C08G 18/75* | (2006.01) | |
| *C08G 73/02* | (2006.01) | |
| *G02C 7/04* | (2006.01) | |

(52) U.S. Cl.
CPC ............. *C08G 18/12* (2013.01); *A61L 27/18* (2013.01); *A61L 29/06* (2013.01); *C08G 18/3203* (2013.01); *C08G 18/3206* (2013.01); *C08G 18/61* (2013.01); *C08G 18/6423* (2013.01); *C08G 18/758* (2013.01); *C08G 73/0233* (2013.01); *G02B 1/043* (2013.01); *A61L 2430/16* (2013.01); *C08G 2210/00* (2013.01); *G02C 7/04* (2013.01)

(58) Field of Classification Search
CPC ...... A61L 27/18; A61L 29/06; A61L 2430/16; C08G 18/12; C08G 18/3203; C08G 18/61; C08G 18/6423; C08G 18/3206; C08G 18/758; C08G 73/0233; C08G 2210/00; G02B 1/043; G02C 7/04
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 4,113,224 A | 9/1978 | Clark et al. |
| 4,197,266 A | 4/1980 | Clark et al. |
| 4,555,732 A | 11/1985 | Tuhro |
| 5,271,875 A | 12/1993 | Appleton et al. |
| 6,444,776 B1 | 9/2002 | Holland et al. |
| 6,517,933 B1 | 2/2003 | Soane et al. |
| 2003/0044468 A1 | 3/2003 | Cellesi et al. |
| 2016/0108180 A1 | 4/2016 | Dias et al. |

FOREIGN PATENT DOCUMENTS

| | | |
|---|---|---|
| EP | 2931790 B1 | 2/2017 |
| WO | 2014093756 A1 | 6/2014 |

OTHER PUBLICATIONS

International Search Report and Written Opinion of the International Searching Authority for PCT/EP2022/056450 dated Jun. 7, 2022, 12 pages.

*Primary Examiner* — Patrick D Niland
(74) *Attorney, Agent, or Firm* — Ryan, Mason & Lewis, LLP

(57) ABSTRACT

A biomedical device is disclosed which is a polymerization product of a mixture comprising (a) one or more difunctional isocyanates; (b) one or more polyalcohols; (c) one or more hydroxy-terminated polysiloxane prepolymers; and (d) one or more polyoxazoline polyols having a weight average molecular weight of equal to or greater than about 1000 Daltons.

21 Claims, No Drawings

BIOMEDICAL DEVICES

PRIORITY CLAIM

The present application claims priority to U.S. Provisional Patent Application Ser. No. 63/161,002, entitled "Biomedical Devices," filed Mar. 15, 2021, the content of which is incorporated by reference herein in its entirety.

BACKGROUND

Biomedical devices such as ophthalmic lenses made from siloxy-containing materials have been investigated for a number of years. Such materials can generally be subdivided into two major classes, namely hydrogels and non-hydrogels. Hydrogels can absorb and retain water in an equilibrium state whereas non-hydrogels do not absorb appreciable amounts of water. Regardless of their water content, both hydrogel and non-hydrogel siloxy and/or fluorinated contact lenses tend to have relatively hydrophobic, non-wettable surfaces.

Hydrogels represent a desirable class of materials for many biomedical applications, including contact lenses and intraocular lenses. Hydrogels are hydrated, crosslinked polymeric systems that contain water in an equilibrium state. Silicone hydrogels are a known class of hydrogels and are characterized by the inclusion of a siloxy-containing material. An advantage of silicone hydrogels over non-silicone hydrogels is that the silicone hydrogels typically have higher oxygen permeability due to the inclusion of the siloxy-containing monomer. Because most existing hydrogels are based on free radical polymerization of monomers containing a crosslinking agent, these materials are thermosetting polymers.

In the field of biomedical devices such as contact lenses, various physical and chemical properties such as, for example, oxygen permeability, wettability, material strength and stability are but a few of the factors that must be carefully balanced in order to provide a useable contact lens. For example, since the cornea receives its oxygen supply from contact with the atmosphere, good oxygen permeability is an important characteristic for certain contact lens materials. Wettability also is important in that, if the lens is not sufficiently wettable, it does not remain lubricated and therefore cannot be worn comfortably in the eye. Accordingly, the optimum contact lens would have at least both excellent oxygen permeability and excellent tear fluid wettability.

SUMMARY

In accordance with an illustrative embodiment, a biomedical device which is a polymerization product of a mixture comprises (a) one or more difunctional isocyanates; (b) one or more polyalcohols; (c) one or more di-hydroxy terminated polysiloxane prepolymers; and (d) one or more polyoxazoline polyols having a weight average molecular weight of equal to or greater than about 1000 Daltons.

In accordance with another illustrative embodiment, a method for making a biomedical device is provided which comprises (a) providing a mixture comprising (i) one or more difunctional isocyanates; (ii) one or more polyalcohols; (iii) one or more di-hydroxy terminated polysiloxane prepolymers; and (iv) one or more polyoxazoline polyols having a weight average molecular weight of equal to or greater than about 1000 Daltons; (b) subjecting the mixture to polymerization conditions to provide a polymerized device, and (c) hydrating the polymerized device.

DETAILED DESCRIPTION

Various illustrative embodiments described herein are directed to biomedical devices obtained from thermoset or thermoplastic polyoxazoline-based, silicone-containing polyurethane materials. The polyoxazoline-based, silicone-containing polyurethane materials described herein in non-limiting illustrative embodiments are particularly suitable for use in the contact lens industry. In addition, the polyoxazoline-based, silicone-containing polyurethane materials are thermoplastic or thermoset materials that exhibit exemplary physical properties, in particular in terms of oxygen permeability and light transmissibility. Advantageously, the thermoplastic or thermoset materials described herein are suitable for use in a conventional molding apparatus, thereby enabling high throughput production of contact lenses.

Thermoplastic polyurethanes have minimal cross-linking; and any bonding in the polymer network is primarily through hydrogen bonding or other physical mechanisms. Because of their lower level of cross-linking, thermoplastic polyurethanes are relatively flexible. The cross-linking bonds in thermoplastic polyurethanes can be reversibly broken by increasing temperature such as during molding or extrusion. That is, the thermoplastic material softens when exposed to heat and returns to its original condition when cooled. On the other hand, thermoset polyurethanes become irreversibly set when they are cured. The cross-linking bonds are irreversibly set and are not broken when exposed to heat. Thus, thermoset polyurethanes, which typically have a high level of cross-linking, are relatively rigid. Accordingly, the term "thermoplastic" as used herein refers to a material which melts at a temperature lower than the temperature at which it degrades. The term "thermoset" as used herein refers to a material which melts at a temperature higher than the temperature at which it degrades.

The biomedical devices disclosed herein are intended for direct contact with body tissue or body fluid. The term "biomedical device" as used herein is any article that is designed to be used while either in or on mammalian tissues or fluid, and preferably in or on human tissue or fluids. Representative examples of biomedical devices include, but are not limited to, artificial ureters, diaphragms, intrauterine devices, heart valves, catheters, denture liners, prosthetic devices, ophthalmic lens applications, where the lens is intended for direct placement in or on the eye, such as, for example, intraocular devices and contact lenses. In an illustrative embodiment, a biomedical device is an ophthalmic device, particularly a contact lens, and more particularly a contact lens made from silicone hydrogels.

As used herein, the term "ophthalmic device" refers to devices that reside in or on the eye. These devices can provide optical correction, wound care, drug delivery, diagnostic functionality or cosmetic enhancement or effect or a combination of these properties. Useful ophthalmic devices include, but are not limited to, ophthalmic lenses such as soft contact lenses, e.g., a soft, hydrogel lens, soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking.

In an illustrative embodiment, an ophthalmic device can be a high-water content ophthalmic device. In an illustrative embodiment, a high-water content ophthalmic device will have an equilibrium water content of at least about 65 weight percent. In another illustrative embodiment, a high-water content ophthalmic device will have an equilibrium water content of at least about 70 weight percent. In another illustrative embodiment, a high-water content ophthalmic device will have an equilibrium water content of at least about 75 weight percent.

In illustrative non-limiting embodiments, the biomedical devices disclosed herein are formed from a polymerization product of a mixture comprising (a) one or more difunctional isocyanates; (b) one or more polyalcohols; (c) one or more hydroxy-terminated polysiloxane prepolymers; and (d) one or more polyoxazoline polyols having a weight average molecular weight of equal to or greater than about 1000 Daltons.

Suitable one or more difunctional isocyanates include, for example, any aliphatic, cycloaliphatic or aromatic isocyanate. Suitable aromatic diisocyanates that may be used herein include, for example, toluene 2,4-diisocyanate (TDI), toluene 2,6-diisocyanate (TDI), 4,4'-methylene diphenyl diisocyanate (MDI), 2,4'-methylene diphenyl diisocyanate (MDI), polymeric methylene diphenyl diisocyanate (PMDI), p-phenylene diisocyanate (PPDI), m-phenylene diisocyanate (PDI), naphthalene 1,5-diisocynate (NDI), naphthalene 2,4-diisocyanate (NDI), p-xylene diisocyanate (XDI), and homopolymers and copolymers and blends thereof. Suitable aliphatic diisocyanates that may be used herein include, for example, isophorone diisocyanate (IPDI), 1,6-hexamethylene diisocyanate (HDI), 4,4'-dicyclohexylmethane diisocyanate ("$H_{12}MDI$"), meta-tetramethylxylene diisocyanate (TMXDI), trans-cyclohexane diisocyanate (CHDI), and homopolymers and copolymers and blends thereof. Suitable multi-functional isocyanates include trimers of HDI or $H_{12}MDI$, oligomers, or other derivatives thereof. The term "difunctional" as used herein means that the average functionality of the isocyanate composition and the polyhydroxy compound is about 2.

In an illustrative embodiment, the one or more difunctional isocyanates are of the formula OCN—$R^1$—NCO, wherein $R^1$ is a linear or branched $C_3$-$C_{18}$-alkylene, an unsubstituted or substituted $C_6$-$C_{10}$-arylene, an unsubstituted or substituted $C_7$-$C_{18}$-aralkylene, an unsubstituted or substituted $C_6$-$C_{10}$-arylene-$C_1$-$C_2$-alkylene-$C_6$-$C_{10}$-arylene, an unsubstituted or substituted $C_3$-$C_8$-cycloalkylene, an unsubstituted or substituted $C_3$-$C_8$-cycloalkylene-$C_1$-$C_6$-alkylene, an unsubstituted or substituted $C_3$-$C_8$-cycloalkylene-$C_1$-$C_6$-alkylene-$C_3$-$C_8$-cycloalkylene or an unsubstituted or substituted $C_1$-$C_6$-alkylene-$C_3$-$C_8$-cyclo-alkylene-$C_1$-$C_6$-alkylene.

In an illustrative embodiment, the one or more difunctional isocyanates can be present in the mixture in an amount ranging from about 20 to about 60 weight percent, based on the total weight of the mixture. In an illustrative embodiment, an amount of the one or more difunctional isocyanates in the mixture can range from about 30 to about 45 weight percent, based on the total weight of the mixture.

The mixture further includes one or more polyalcohols. Suitable polyalcohols include, for example, straight or branched, aliphatic or aromatic diols, triols, higher functional polyols that have an average functionality of greater than three, tertiary amine polyalcohols, alkoxylated polyalcohols, polyether polyalcohols, and mixtures thereof. In an illustrative embodiment, the one or more polyalcohols can have, for example, from about 2 to about 1000 carbon atoms and from 2 to about 10 hydroxy groups. In another embodiment, the one or more polyalcohols can have up to about 1000 carbon atoms, or up to about 750 carbon atoms, or up to about 650 carbon atoms, or up to about 550 carbon atoms, or up to about 450 carbon atoms, or up to about 350 carbon atoms, or up to about 250 carbon atoms, or up to about 150 carbon atoms, or up to about 100 carbon atoms, or up to about 50 carbon atoms, and from 2 to about 10 hydroxy groups. In one embodiment, the one or more polyalcohols can have at least 2 carbon atoms, or at least about 5 carbon atoms, or at least about 10 carbon atoms, or at least about 15 carbon atoms, or at least about 20 carbon atoms, or at least about 25 carbon atoms, or at least about 30 carbon atoms, or at least about 40 carbon atoms, or at least about 50 carbon atoms, or at least about 100 carbon atoms, and from 2 to about 10 hydroxy groups. As one skilled in the art will readily appreciate, any of the foregoing lower limits can be combined with any of the upper limits.

In an illustrative embodiment, the one or more polyalcohols can have, for example, from about 1 to about 50 carbon atoms and from 2 to 10 hydroxy groups. In an illustrative embodiment, the one or more polyalcohols can have, for example, from about 2 to about 50 carbon atoms and from 2 to 10 hydroxy groups. When used as a chain extender, the one or more polyalcohols can have, for example, from about 2 to about 20 carbon atoms, or from about 2 to about 10 carbon atoms or from about 2 to about 5 carbon atoms, and from 2 to 10 hydroxy groups or from 2 to 4 hydroxy groups.

Suitable diols include, for example, ethylene glycol, diethylene glycol, triethylene glycol, propylene glycol, dipropylene glycol, trimethylene glycol, butylene glycols, neopentyl glycol, 2,2-dimethyl-1,3 propane diol, 1,6-hexanediol, 2-methyl-1,3-propanediol, 1,3-propane glycol, 1,3-butanediol, 1,4-butanediol, 1,5-pentanediol, 3-hydroxy-2,2-dimethylpropyl-3-hydroxy-2,2-dimethyl propanoate (HPHP), 1,2-cyclohexanediol, 1,3-cyclohexanediol, 1,3-cyclohexanedimethanol, 1,4-cyclohexanedimethanol, resorcinol, hydroquinone, and poly(oxyalkylene) polyols derived by the condensation of ethylene oxide, propylene oxide, or a combination thereof. Mixtures of any of the diols are also contemplated. The polyalcohol component can also include triols, higher functional polyols that have an average functionality of greater than three, or mixtures thereof.

Suitable triols and higher functional polyalcohols include, for example, glycerol, diglycerol, trimethylolpropane, pentaerythritol, dipentaerythritol, sugars, such as sucrose, glucose, and fructose; sugar alcohols, such as sorbitol and mannitol, and combinations of any of the foregoing. A mixture of diols, triols, and/or higher functional polyalcohols is also contemplated for some embodiments.

Suitable tertiary amine polyalcohols include, for example, compounds having at least two hydroxyls and at least one tertiary amine group. In one embodiment, a tertiary amine polyalcohol can have, for example, from about 2 to about 50 carbon atoms, or from about 2 to about 20 carbon atoms, or from about 2 to about 10 carbon atoms, or from about 2 to about 5 carbon atoms, and from 2 to 10 hydroxy groups or from 2 to 4 hydroxy groups. Representative examples of suitable tertiary amine polyalcohols include triethanolamine, N-methyldiethanolamine, N-ethyldiethanolamine, N-propyldiethanolamine N-n-butyldiethanolamine N-tert-butyldiethanolamine N-bis(2-hydroxyethyl)octadecylamine, bis(2-hydroxyethyl) cocoalkylamines, bis(2-hydroxyethyl)oleylamine, ethoxylated (EO), propoxylated (PO) and mixed EO/PO tertiary amines such as ethoxylated triethanolamine, and the like and mixtures thereof.

Suitable alkoxylated polyalcohols can have, for example, from about 2 to about 20 carbon atoms, or from about 3 to about 20 carbon atoms from about 4 to about 20 carbon atoms or from about 2 to about 10 carbon atoms, and from 2 to 10 hydroxy groups or from 2 to 4 hydroxy groups. In one embodiment, the alkoxylated polyalcohols can have a number average molecular weight of 200 to 5,000 grams/mole. In one embodiment, suitable alkoxylated polyalcohols can be polyoxyethylene glycols, i.e., "PEGs" which are used to describe polyoxyethylene and may be followed by a number that indicates a PEG moiety with the approximate molecular weight equal to the number. Representative examples of PEGs for use herein include PEG350, PEG4000, PEG6000, PEG8000 and PEG10000 (which is a PEG moiety having an approximate molecular weight of 10,000 Daltons).

Representative examples of suitable alkoxylated polyalcohols include ethoxylated diols, ethoxylated triols, ethoxylated tetrols, ethoxylated pentaols, ethoxylated hexaols, propoxylated diols, propoxylated triols, propoxylated tetrols, propoxylated pentaols, propoxylated hexaols butoxylated diols, butoxylated triols, butoxylated tetrols, butoxylated pentaols, butoxylated hexaols, and the like. Representative examples of ethoxylated polyalcohols are ethoxylated glycerol, ethoxylated pentaerythritol, ethoxylated trimethylolpropane, ethoxylated glucoside, and ethoxylated glucose.

Suitable polyether polyalcohols include, for example, polyether polyalcohols comprising one or more chains or polymeric components which have one or more (—O—R—) repeats units wherein R is an alkylene or arylene group having 2 to about 6 carbon atoms. The polyethers may be derived from block copolymers formed from different ratio components of ethylene oxide (EO) and propylene oxide (PO). Such polyethers and their respective component segments may include different attached hydrophobic and hydrophilic chemical functional group moieties and segments.

In an embodiment, a representative example of a suitable polyether polyalcohol is a poloxamer block copolymer. One specific class of poloxamer block copolymers are those available under the trademark Pluronic© (BASF Wyandotte Corp., Wyandotte, Mich.). Poloxamers include Pluronics and reverse Pluronics. Pluronics are a series of ABA block copolymers composed of poly(ethylene oxide)-poly(propylene oxide)-poly(ethylene oxide) blocks as generally represented in Formula (I):

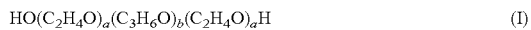

HO(C$_2$H$_4$O)$_a$(C$_3$H$_6$O)$_b$(C$_2$H$_4$O)$_a$H (I)

wherein a is independently at least 1 and b is at least 1.

Reverse Pluronics are a series of BAB block copolymers, respectively composed of poly(propylene oxide)-poly(ethylene oxide)-poly(propylene oxide) blocks as generally represented in Formula (II):

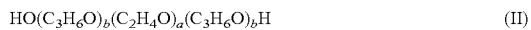

HO(C$_3$H$_6$O)$_b$(C$_2$H$_4$O)$_a$(C$_3$H$_6$O)$_b$H (II)

wherein a is at least 1 and b is independently at least 1. The poly(ethylene oxide), PEO, blocks are hydrophilic, whereas the poly(propylene oxide), PPO, blocks are hydrophobic in nature. The poloxamers in each series have varying ratios of PEO and PPO which ultimately determines the hydrophilic-lipophilic balance (HLB) of the material, i.e., the varying HLB values are based upon the varying values of a and b, a representing the number of hydrophilic poly(ethylene oxide) units (PEO) being present in the molecule and b representing the number of hydrophobic poly(propylene oxide) units (PPO) being present in the molecule.

Another example of a suitable polyether polyalcohol which can be a poloxamine block copolymer. The term block copolymer as used herein shall be understood to mean a poloxamer and/or poloxamine as having two or more blocks in their polymeric backbone(s). While the poloxamers and reverse poloxamers are considered to be difunctional molecules (based on the terminal hydroxyl groups), the poloxamines are in a tetrafunctional form, i.e., the molecules are tetrafunctional block copolymers terminating in primary hydroxyl groups and linked by a central diamine. One specific class of poloxamine block copolymers are those available under the trademark Tetronic (BASF). Poloxamines include Tetronic and reverse Tetronics. Poloxamines have the following general structure of Formula (III):

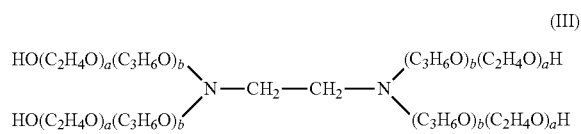

wherein a is independently at least 1 and b is independently at least 1.

The foregoing one or more polyalcohols can be present in the mixture in an amount ranging from about 10 to about 70 weight percent, based on the total weight of the mixture. In an illustrative embodiment, an amount of the one or more polyalcohols in the mixture can range from about 12 to about 20 weight percent, based on the total weight of the mixture.

The mixture further includes one or more hydroxy-terminated polysiloxane prepolymers. In an illustrative embodiment, a hydroxy-terminated polysiloxane prepolymer is represented by the structure of Formula (IV):

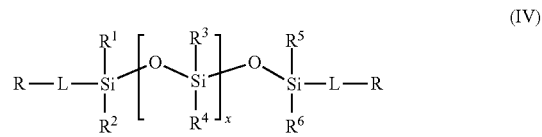

wherein each R is independently a hydroxyl-containing reactive functional end group, $R^1$ to $R^6$ are independently a hydrocarbyl group such as, for example, a straight or branched, substituted or unsubstituted $C_1$-$C_{30}$ alkyl group, a substituted or unsubstituted $C_3$-$C_{30}$ cycloalkyl group, a substituted or unsubstituted $C_4$-$C_{30}$ cycloalkylalkyl group, a substituted or unsubstituted $C_3$-$C_{30}$ cycloalkenyl group, a substituted or unsubstituted $C_6$-$C_{30}$ aryl group, and a substituted or unsubstituted $C_7$-$C_{30}$ arylalkyl group, L is independently a linking group and x is from 3 to 200.

A hydroxyl-containing reactive functional end group for use herein is a group containing at least one hydroxyl group. Representative examples of hydroxyl-containing reactive functional end groups for use herein include, by way of example, a group having the following general formula —$R^7$(OH) wherein $R^7$ is independently an alkyl group, aryl group, and cycloalkyl group as defined herein and the like.

Linking group L is independently a straight or branched, substituted or unsubstituted alkyl group, a substituted or unsubstituted cycloalkyl group, a substituted or unsubstituted aryl group, a substituted or unsubstituted ether or polyether group, and a substituted or unsubstituted ester group.

Representative examples of alkyl groups for use herein include, by way of example, a straight or branched alkyl chain radical containing carbon and hydrogen atoms of from 1 to about 30 carbon atoms or from 1 to about 12 carbon atoms or from 1 to about 6 carbon atoms with or without unsaturation, to the rest of the molecule, e.g., methyl, ethyl, n-propyl, 1-methylethyl (isopropyl), n-butyl, n-pentyl, methylene, ethylene, etc., and the like.

Representative examples of cycloalkyl groups for use herein include, by way of example, a substituted or unsubstituted non-aromatic mono or multicyclic ring system of about 3 to about 30 carbon atoms or from 3 to about 6 carbon atoms such as, for example, cyclopropyl, cyclobutyl, cyclopentyl, cyclohexyl, perhydronapththyl, adamantyl and norbornyl groups, bridged cyclic groups or sprirobicyclic groups, e.g., spiro-(4, 4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 4 to about 30 carbon atoms or from 3 to about 6 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 30 carbon atoms or from 3 to about 6 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 6 to about 30 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined herein directly bonded to an alkyl group as defined herein, e.g., —$CH_2C_6H_5$, —$C_2H_4C_6H_5$ and the like, wherein the aryl group can optionally contain one or more heteroatoms, e.g., O and N, and the like.

Representative examples of ester groups for use herein include, by way of example, a carboxylic acid ester having 1 to 20 carbon atoms and the like.

Representative examples of ether or polyether containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are as defined herein. Exemplary ether or polyether-containing groups include, by way of example, alkylene oxides, poly(alkylene oxide)s such as ethylene oxide, propylene oxide, butylene oxide, poly(ethylene oxide)s, poly(ethylene glycol)s, poly(propylene oxide)s, poly(butylene oxide)s and mixtures or copolymers thereof, an ether or polyether group of the general formula —$(R^{14}OR^{15})_t$, wherein $R^{14}$ is a bond, a substituted or unsubstituted alkyl, cycloalkyl or aryl group as defined herein and $R^{15}$ is a substituted or unsubstituted alkyl, cycloalkyl or aryl group as defined herein and t is at least 1, and the like.

In an illustrative embodiment, a hydroxy-terminated polysiloxane prepolymer is represented by the structure of Formula (V):

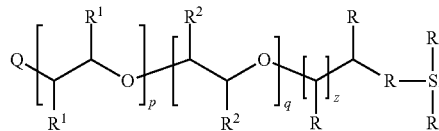 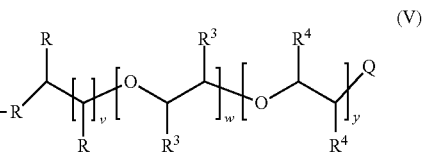

(V)

wherein each R, $R_1$, $R^2$, $R^3$ and $R^4$ group independently represents H or a hydrocarbyl group such as, for example, a straight or branched, substituted or unsubstituted $C_1$-$C_{12}$ alkyl group; p is an integer from 0 to 40, e.g., 1 to 10; q is an integer from 0 to 40, e.g., 1 to 10; z is an integer from 2 to 50, e.g., 2 to 10 or 2; u is an integer from 1 to 100, e.g., 10 to 40; y is an integer from 0 to 40, e.g., 1 to 10; w is an integer from 0 to 40, e.g., 1 to 10; v is an integer from 2 to 50, e.g., 2 to 10; and each Q group independently represents a hydroxyl-containing reactive functional end group.

In an illustrative embodiment, at least one $R^1$ group represents a hydrocarbyl group and p represents an integer of from 1 to 40, or at least one $R^2$ group represents a hydrocarbyl group and q represents an integer of from 1 to 40; and at least one $R^3$ group represents a hydrocarbyl group and w represents an integer of from 1 to 40, or at least one $R^4$ group represents a hydrocarbyl group and y represents an integer of from 1 to 40.

In an illustrative embodiment, each R, $R^1$, $R^2$, $R^3$ and $R^4$ group independently represents H or an alkyl group such as a methyl, ethyl or propyl group.

In an illustrative embodiment, at least one $R^1$ group and at least one $R^4$ group represent a hydrocarbyl group; p represents an integer of from 1 to 40 and y represents an integer of from 1 to 40.

In an illustrative embodiment, at least one $R^2$ group and at least one $R^3$ group represent a hydrocarbyl group; q represents an integer of from 1 to 40 and w represents an integer of from 1 to 40.

In an illustrative embodiment, the silicone-containing compound is symmetrical but non symmetric structures bearing silicone compounds may also be employed.

In an illustrative embodiment, where $R^1$ and/or $R^4$ represent a hydrocarbyl group, p and q independently represent an integer of from 1 to 5 respectively, and w and y independently represent an integer of from 1 to 10, or from 5 to 10, respectively.

In an illustrative embodiment, where $R^3$ and/or $R^4$ represent a hydrocarbyl group, w and y independently represent an integer of from 1 to 5, respectively, and p and q independently represent an integer of from 1 to 10, or from 5 to 10, respectively.

In an illustrative embodiment, Q is OH.

In another illustrative embodiment, a hydroxy-terminated polysiloxane prepolymer is represented by the structure of Formula (Va):

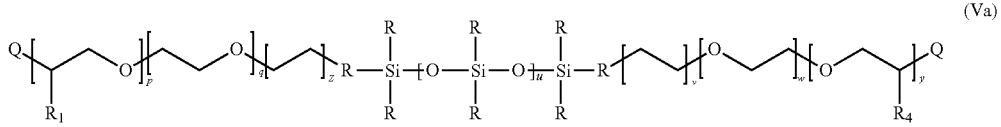

wherein $R_1$ and $R_4$ represent a hydrocarbyl group, e.g., a straight or branched, substituted or unsubstituted $C_1$-$C_{12}$ alkyl group such as methyl, ethyl or propyl; p represents an integer from 1 to 40, e.g., from 1 to 10; y represents an integer from 1 to 40, e.g., from 1 to 10; q represents an integer from 1 to 40, e.g., from 5 to 10; w represents an integer from 1 to 40, e.g., from 5 to 10; and Q, z, R, u and v are as defined above.

In another illustrative embodiment, a hydroxy-terminated polysiloxane prepolymer is represented by the structure of Formula (Vb):

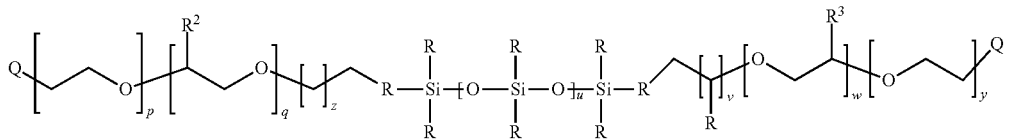

wherein $R^2$ and $R^3$ represent a hydrocarbyl group, e.g., a straight or branched, substituted or unsubstituted $C_1$-$C_{12}$ alkyl group such as methyl, ethyl or propyl; p represents an integer from 1 to 40, e.g., from 1 to 10; y represents an integer from 1 to 40, e.g., from 1 to 10; q represents an integer from 1 to 40, e.g., from 5 to 10; w represents an integer from 1 to 40, e.g., from 5 to 10; and Q, z, R, u and v are as defined above.

In another illustrative embodiment, a hydroxy-terminated polysiloxane prepolymer is represented by the structure of Formula (Vc):

HO—(CH($R_1$)CH$_2$O)$_p$—(CH$_2$CH$_2$O)$_q$—(CH$_2$)$_z$—Si ($R_1$)$_2$—(OSi($R_1$)$_2$)$_u$—O—Si($R_1$)$_2$(CH$_2$)$_v$—

(OCH$_2$CH$_2$)$_w$—(OCH$_2$CH($R_1$))$_y$—OH (Vc)

where each $R_1$ group is an alkyl group, such as methyl, ethyl or propyl, and p, q, z, u, v, w and y are as defined above. One example of a compound of formula (Vc) is Silsurf® 2510 available from Siltech Corporation where each $R_1$ group represents a methyl group, z is 25, p is 10 and y is 10.

In an illustrative embodiment, the one or more hydroxy-terminated polysiloxane prepolymers can have a number average molecular weight of about 500 to about 5000 Daltons as determined by, for example, size-exclusion chromatography (i.e., gel permeation chromatography). In an illustrative embodiment, the one or more hydroxy-terminated polysiloxane prepolymers can have a number average molecular weight of about 500 to about 3500 Daltons. In an illustrative embodiment, the one or more hydroxy-terminated polysiloxane prepolymers can have a number average molecular weight of about 800 to about 3000 Daltons.

Methods for making the one or more hydroxy-terminated polysiloxane prepolymers are well known and within the purview of one skilled in the art. In addition, the polysiloxane prepolymers are also commercially available from such sources as, for example, Gelest, Silar, Shin-Etsu, Momentive and Siltech.

The one or more hydroxy-terminated polysiloxane prepolymers can be present in the mixture in an amount ranging from about 3 to about 60 weight percent, based on the total weight of the mixture. In an illustrative embodiment, an amount of the one or more hydroxy-terminated polysiloxane prepolymers in the mixture can range from about 10 to about 50 weight percent, based on the total weight of the mixture.

The mixture further includes one or more polyoxazoline polyols having a weight average molecular weight of equal to or greater than about 1000 Daltons as determined by, for example, size-exclusion chromatography (i.e., gel permeation chromatography). In an illustrative embodiment, the one or more polyoxazoline polyols can have a weight average molecular weight of equal to or greater than about 1000 Daltons and up to about 50,000,000 Daltons. In an illustrative embodiment, the one or more polyoxazoline polyols can have a weight average molecular weight of equal to or greater than about 1000 Daltons, or greater than 10,000 Daltons, or greater than 25,000 Daltons, or greater than 50,000 Daltons, or greater than 100,000 Daltons, or greater than 250,000 Daltons, or greater than 500,000 Daltons, or greater than 750,000 Daltons, or greater than 1,000,000 Daltons, or greater than 2,500,000 Daltons, or greater than 5,000,000 Daltons, or greater than 10,000,000 Daltons, or greater than 25,000,000 Daltons and up to about 50,000,000 Daltons. In an illustrative embodiment, the one or more polyoxazoline polyols can have a weight average molecular weight of less than about 50,000,000 Daltons, or less than 25,000,000 Daltons, or less than 10,000,000 Daltons, or less than 5,000,000 Daltons, or less than 2,500,000 Daltons, or less than 1,000,000 Daltons, or less than 750,000 Daltons, or less than 500,000 Daltons, or less than 250,000 Dalton, or less than 100,000 Daltons.

In an illustrative embodiment, the one or more polyoxazoline polyols are di-functional, tri-functional or tetra-functional polyoxazoline polyols. In an illustrative embodiment, a di-functional polyoxazoline polyol is one of a $C_1$-$C_{12}$ alkyl polyoxazoline polyol having two oxazoline-containing hydroxyl groups per alkyl molecule with the alkyl molecule optionally containing one or more of ether and/or ester linkages, a $C_6$-$C_{30}$ aromatic polyoxazoline polyol having two oxazoline-containing hydroxyl groups per aromatic molecule and a $C_3$-$C_{20}$ cycloalkyl polyoxazoline polyol having two oxazoline-containing hydroxyl groups per cycloalkyl molecule. In one embodiment, the aryl group is phenyl. For example, in one embodiment, the one or more polyoxazoline polyols is represented by the structure of Formula (VI):

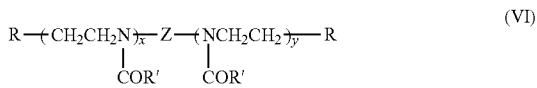
(VI)

wherein each R is a hydroxyl group; each R' is independently a hydrocarbyl group such as, for example, an alkyl group, a haloalkyl group, an alkene group, an alkyne group, a cycloalkyl group, a halocycloalkyl group, an aryl group, a haloaryl group, an aralkyl group and a haloaralkyl group; Z is a divalent linkage and each of x and y are independently at least 1, e.g., from 1 and up to about 200. Representative Z linkages include a single bond, a $C_1$-$C_{12}$ alkylene group optionally including ether linkages, a $C_6$-$C_{30}$ arylene group, a $C_7$-$C_{30}$ alkarylene group, and a $C_3$-$C_{20}$ cycloalkylene group.

In another illustrative embodiment, a tri-functional polyoxazoline polyol is a $C_1$-$C_{12}$ alkyl polyoxazoline polyol having three oxazoline-containing hydroxyl groups per alkyl molecule with the alkyl molecule optionally containing one or more of ether and/or ester linkages. In an illustrative embodiment, a $C_1$-$C_{12}$ alkyl molecule can be a straight or branched alkyl chain molecule containing carbon and hydrogen atoms of from 1 to 12 carbon atoms or from 1 to about 6 carbon atoms with or without unsaturation, to the rest of the molecule. The three oxazoline-containing hydroxyl groups can be the same or different and provided at any point of attachment to the alkyl molecule.

In another illustrative embodiment, a tri-functional polyoxazoline polyol is a $C_6$-$C_{30}$ aromatic polyoxazoline polyol having three oxazoline-containing hydroxyl groups per aromatic molecule. In an illustrative embodiment, a $C_6$-$C_{30}$ aromatic can be a substituted or unsubstituted monoaromatic or polyaromatic radical containing from about 6 to about 30 carbon atoms or from 6 to 12 carbon atoms such as, for example, phenyl, naphthyl, tetrahydronapthyl, indenyl, biphenyl and the like, optionally containing one or more heteroatoms, e.g., O and N. The three oxazoline-containing hydroxyl groups can be the same or different and provided at any point of attachment to the aromatic molecule(s). In one embodiment, the aromatic molecule is phenyl.

In another illustrative embodiment, a tri-functional polyoxazoline polyol is a $C_3$-$C_{20}$ cycloalkyl polyoxazoline polyol having three oxazoline-containing hydroxyl groups per cycloalkyl molecule. In an illustrative embodiment, a $C_3$-$C_{20}$ cycloalkyl molecule can be a substituted or unsubstituted non-aromatic mono or multicyclic ring system of about 3 to about 20 carbon atoms or from 3 to about 6 carbon atoms such as, for example, cyclopropyl, cyclobutyl, cyclopentyl, cyclohexyl, perhydronapththyl, adamantyl and nor-bornyl groups, bridged cyclic groups or sprirobicyclic groups, e.g., spiro-(4, 4)-non-2-yl and the like, optionally containing one or more heteroatoms, e.g., O and N. The three oxazoline-containing hydroxyl groups can be the same or different and provided at any point of attachment to the cycloalkyl molecule.

In another illustrative embodiment, a tetra-functional polyoxazoline polyol is one of a $C_1$-$C_{12}$ alkyl polyoxazoline polyol having four oxazoline-containing hydroxyl groups per alkyl molecule with the alkyl molecule optionally containing one or more of ether and/or ester linkages, a $C_6$-$C_{30}$ aromatic polyoxazoline polyol having four oxazoline-containing hydroxyl groups per aromatic molecule and a $C_3$-$C_{20}$ cycloalkyl polyoxazoline polyol having four oxazoline-containing hydroxyl groups per cycloalkyl molecule. In one embodiment, the aryl group is phenyl. The $C_1$-$C_{12}$ alkyl molecule, $C_6$-$C_{30}$ aromatic molecule and $C_3$-$C_{20}$ cycloalkyl molecule can be any of those described above. In an illustrative embodiment, the four oxazoline-containing hydroxyl groups can be the same or different and provided at any point of attachment to the alkyl molecule, aromatic molecule and cycloalkyl molecule.

The foregoing one or more polyoxazoline polyols having a weight average molecular weight of equal to or greater than about 1000 Daltons can be prepared by methods known in the art.

In one embodiment, the foregoing one or more polyoxazoline polyols can be obtained by subjecting a 2-substituted-2-oxazoline (A-1) to catalyzed ring opening polymerization,

(A-1)

using, for example, an initiator such as a bromo-containing initiator (A-2),

(A-2)

wherein Z is a hydrocarbyl group and a is an integer from 2 to 4, followed by reaction of the resultant product with a water/sodium carbonate mixture or other suitable terminating agents to prepare the polyoxazoline polyols. The Z hydrocarbyl group of the bromo-containing initiator can be any $C_1$-$C_{30}$ alkyl group, $C_6$-$C_{30}$ aromatic group, $C_3$-$C_{20}$ cycloalkyl, $C_1$-$C_{20}$ ester-containing group, $C_1$-$C_{20}$ polyether-containing group, and the like. The $C_1$-$C_{30}$ alkyl group, $C_6$-$C_{30}$ aromatic group, $C_3$-$C_{20}$ cycloalkyl, $C_1$-$C_{20}$ ester-containing group, and $C_1$-$C_{20}$ polyether-containing group can be any of those described hereinabove. Suitable terminating agents other than a water/sodium carbonate mixture can be used including, for example, glycolic acid, lactic acid, ethylene glycol, propylene glycol, etc., in the presence of a base such as triazabicyclodecene.

In an illustrative embodiment, the foregoing one or more polyoxazoline polyols can be obtained by subjecting a 2-substituted-2-oxazoline (A-1) to the catalyzed ring opening polymerization process as set forth below.

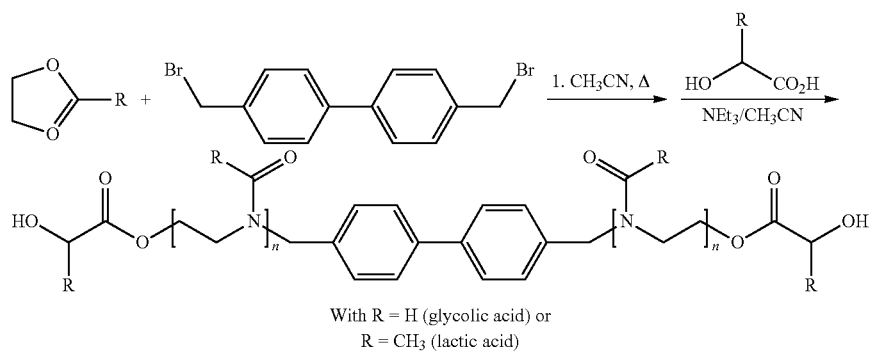

With R = H (glycolic acid) or
R = CH₃ (lactic acid)

In another illustrative embodiment, the foregoing one or more polyoxazoline polyols can be obtained by subjecting a 2-substituted-2-oxazoline (A-1) to the catalyzed ring opening polymerization process as set forth below.

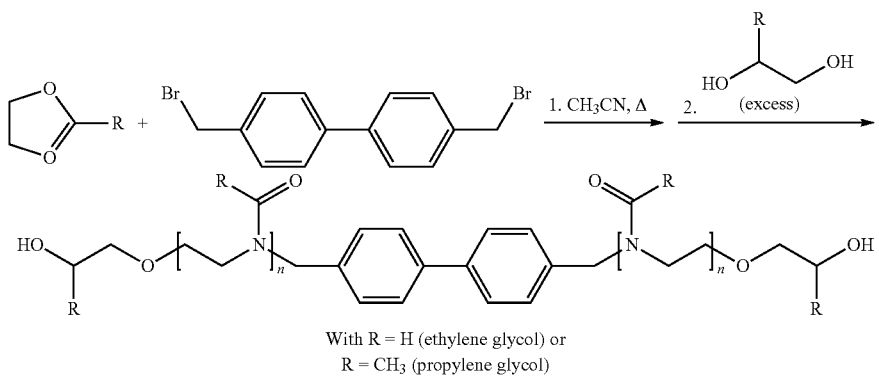

With R = H (ethylene glycol) or
R = CH₃ (propylene glycol)

Accordingly, a suitable alkyl-substituted oxazoline for use herein is a 2-alkyl-substituted oxazoline represented by the following formula:

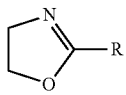

where R is an alkyl group of 1 to 12 carbon atoms. In an illustrative non-limiting embodiment, a 2-alkyl-substituted oxazoline for use herein is 2-isopropenyl-2-oxazoline. Thus, in illustrative embodiments, the poly(2-alkyloxazoline) repeating units as shown above in the catalyzed ring opening polymerization processes are represented as follows:

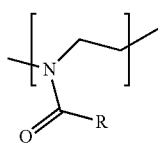

where R is an alkyl group of 1 to 12 carbon atoms.

The one or more polyoxazoline polyols can be present in the mixture in an amount ranging from about 5 to about 65 weight percent, based on the total weight of the mixture. In an illustrative embodiment, an amount of the one or more polyoxazoline polyols in the mixture can range from about 10 to about 45 weight percent, based on the total weight of the mixture.

In an illustrative embodiment, the mixture will further contain a catalyst for carrying out the reaction to prepare the polymerization product. Suitable urethane catalysts include, for example, the stannous salts of carboxylic acids, such as stannous octoate, stannous oleate, stannous acetate, and stannous laurate, dialkyltin dicarboxylates, such as dibutyltin dilaurate and dibutyltin diacetate which are known in the art as urethane catalysts, as are tertiary amines and tin mercaptides.

The amount of catalyst employed is generally between about 0.005 and about 5 weight percent of the mixture catalyzed, depending on the nature of the isocyanate.

The mixture may further contain other monomers. In an illustrative embodiment, the mixture can further include one or more antioxidants. Suitable antioxidants can be any of those generally used for polyurethanes such as, for example, BHA (butylated hydroxyl anisole), BHT (butylated hydroxytoluene) and ascorbic acid etc. The one or more antioxidants can be used in an amount of about 0.01 to about 10 weight percent, or from about 0.1 to about 5 weight percent, or from about 0.2 to about 1 weight percent, based on the total weight of the mixture.

In another illustrative embodiment, the mixture can further include one or more end terminal functionalized surfactants. A suitable end terminal functionalized surfactant includes, by way of example, the poloxamers such as Pluronics and reverse Pluronics, and the poloxamines such as Tetronic and reverse Tetronics as discussed hereinabove.

The poloxamers and reverse poloxamers have terminal hydroxyl groups that can be terminal functionalized. An example of a terminal functionalized poloxamer is a poloxamer dimethacrylate (e.g., Pluronic® F127 dimethacrylate) as disclosed in U.S. Patent Application Publication No. 2003/0044468. Other examples include glycidyl-terminated copolymers of polyethylene glycol and polypropylene glycol as disclosed in U.S. Pat. No. 6,517,933.

The poloxamer and/or poloxamine can be functionalized to provide the desired reactivity at the end terminal of the molecule. The functionality can be varied and is determined based upon the intended use of the functionalized PEO- and PPO-containing block copolymers. That is, the PEO- and PPO-containing block copolymers are reacted to provide end terminal functionality that is complementary with the intended device forming mixture.

Representative examples of reaction sequences by which PEO- and PPO-containing block copolymers can be end-functionalized are provided below.

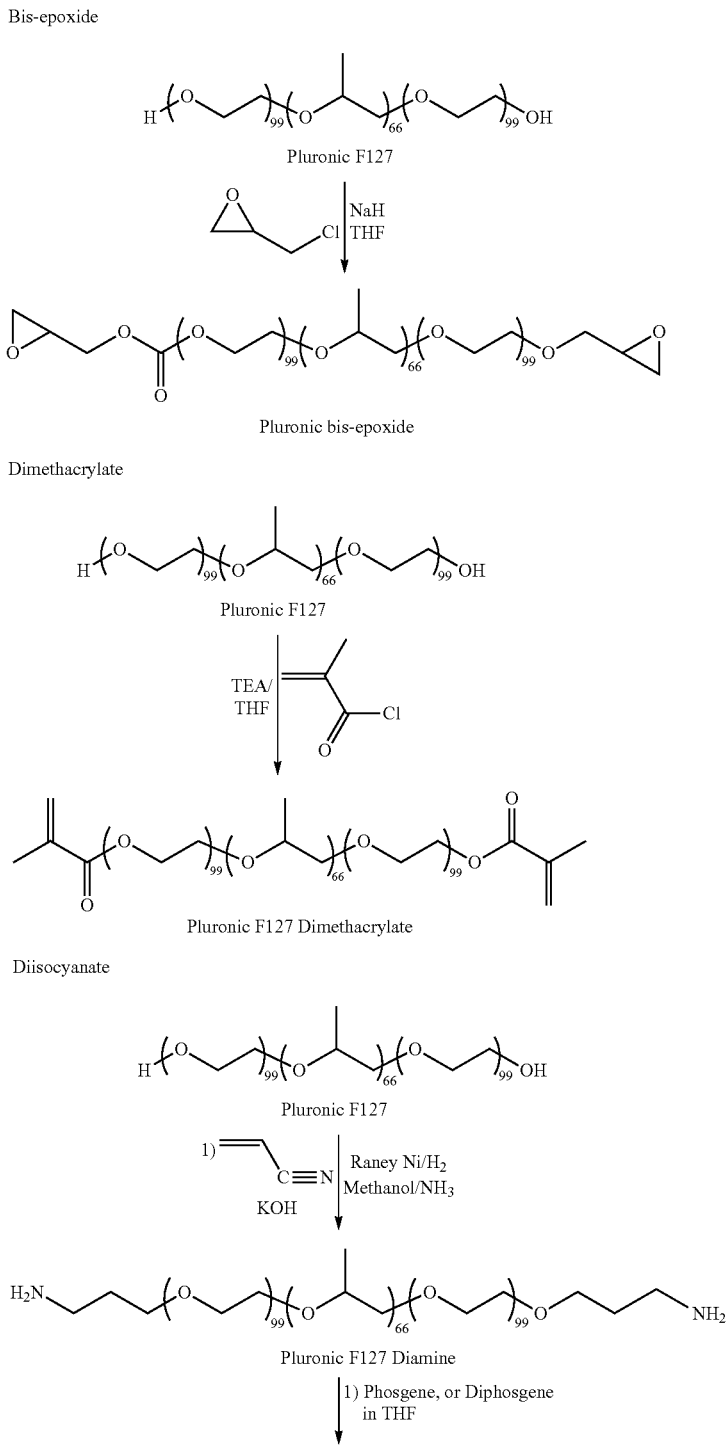

-continued

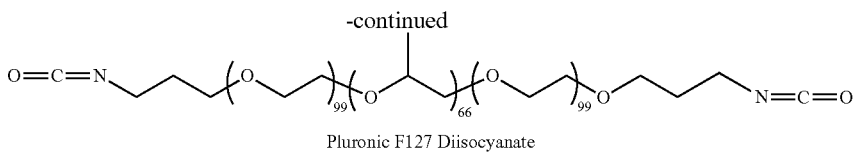

Pluronic F127 Diisocyanate

The foregoing reaction sequences are merely exemplary, but non-limiting, examples of reactions for providing functionalized termini for PEO- and PPO-containing block copolymers. It is to be understood that one of ordinary skill in the art would be able to determine other reaction methods without engaging in an undue amount of experimentation. It should also be understood that any particular block copolymer molecule shown is only one chain length of a polydispersed population of the referenced material.

In one embodiment, an end terminal functionalized surfactant is selected from the group consisting of poloxamers having at least one end terminal functionalized, reverse poloxamers having at least one end terminal functionalized, poloxamines having at least one end terminal functionalized, reverse poloxamines having at least one end terminal functionalized and mixtures thereof.

Generally, the end terminal functionalized surfactants will be present in the mixtures in an amount ranging from about 0.01 to about 20 weight percent, or from about 1 to about 10 weight percent, or from about 3 to about 6 weight percent, based on the total weight of the mixture.

The mixture may further contain, as necessary and within limits not to impair the purpose and effect of the illustrative embodiments disclosed herein, various additives such as, for example, one or more ultraviolet (UV) blockers, coloring agents, lubricant internal wetting agents, toughening agents and the like and other constituents as is well known in the art.

The biomedical devices of the illustrative embodiments, e.g., contact lenses or intraocular lenses, can be prepared by polymerizing the foregoing mixtures to form a product that can be subsequently formed into the appropriate shape by, for example, lathing, injection molding, compression molding, cutting and the like. For example, in producing contact lenses, the initial mixture may be polymerized in tubes to provide rod-shaped articles, which are then cut into buttons. The buttons may then be lathed into contact lenses.

Alternately, the biomedical devices such as contact lenses may be cast directly in molds, e.g., polypropylene molds, from the mixtures, e.g., by spincasting and static casting methods. Spincasting methods are disclosed in U.S. Pat. Nos. 3,408,429 and 3,660,545, and static casting methods are disclosed in U.S. Pat. Nos. 4,113,224, 4,197,266, and 5,271,875. Spincasting methods involve charging the mixtures to be polymerized to a mold, and spinning the mold in a controlled manner while exposing the mixture to a radiation source such as UV light. Static casting methods involve charging the mixture between two mold sections, one mold section shaped to form the anterior lens surface and the other mold section shaped to form the posterior lens surface, and curing the mixture while retained in the mold assembly to form a lens. U.S. Pat. No. 5,271,875 describes a static cast molding method that permits molding of a finished lens in a mold cavity defined by a posterior mold and an anterior mold. As an additional method, U.S. Pat. No. 4,555,732 discloses a process where an excess of a mixture is cured by spincasting in a mold to form a shaped article having an anterior lens surface and a relatively large thickness, and the posterior surface of the cured spincast article is subsequently lathed to provide a contact lens having the desired thickness and posterior lens surface.

Polymerization can be performed in a reaction medium, such as, for example, a solution or dispersion using a suitable solvent. Generally, polymerization can be carried out for about 15 minutes to about 72 hours. If desired, the resulting polymerization product can be dried under vacuum, e.g., for about 5 to about 72 hours or left in an aqueous solution prior to use.

Polymerization of the mixtures will yield a polymer, that when hydrated, preferably forms a hydrogel. When producing a hydrogel lens, the mixture may further include at least a diluent, e.g., a PEG-ether diluent, that is ultimately replaced with water when the polymerization product is hydrated to form a hydrogel. The maximum amount of diluent which may be used will depend on the amount of swelling the diluent causes the final polymers. Excessive swelling will or may cause the copolymer to collapse when the diluent is replaced with water upon hydration. Generally, the water content of the hydrogel is as described hereinabove. The amount of diluent used should be less than about 50 weight percent and in most cases, the diluent content will be less than about 30 weight percent. However, in a particular polymer system, the actual limit will be dictated by the solubility of the various monomers in the diluent. In order to produce an optically clear copolymer, it is important that a phase separation leading to visual opacity does not occur between the comonomers and the diluent, or the diluent and the final copolymer.

If necessary, it may be desirable to remove residual diluent from the lens before edge-finishing operations which can be accomplished by evaporation at or near ambient pressure or under vacuum. An elevated temperature can be employed to shorten the time necessary to evaporate the diluent. The time, temperature and pressure conditions for the solvent removal step will vary depending on such factors as the volatility of the diluent and the specific monomeric components, as can be readily determined by one skilled in the art. If desired, the mixture used to produce the hydrogel lens may further include crosslinking and wetting agents known in the prior art for making hydrogel materials.

The biomedical devices such as contact lenses obtained herein may be subjected to optional machining operations. For example, the optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

The lens may then be transferred to individual lens packages containing a buffered saline solution. The saline solution may be added to the package either before or after transfer of the lens. Appropriate packaging designs and materials are known in the art. A plastic package is releasably sealed with a film. Suitable sealing films are known in the art and include foils, polymer films and mixtures thereof. The sealed packages containing the lenses are then sterilized to ensure a sterile product.

As one skilled in the art will readily appreciate other steps may be included in the molding and packaging process described above. Such other steps can include, for example, coating the formed lens, surface treating the lens during formation (e.g., via mold transfer), inspecting the lens, discarding defective lenses, cleaning the mold halves, reusing the mold halves, and the like and combinations thereof.

The following examples are provided to enable one skilled in the art to practice the invention and are merely illustrative. The examples should not be read as limiting the scope of the invention as defined in the claims.

Example 1

A polyoxazoline having a number average molecular weight of 400 Daltons and a weight average molecular weight of 1900 Daltons was prepared according to the following reaction scheme.

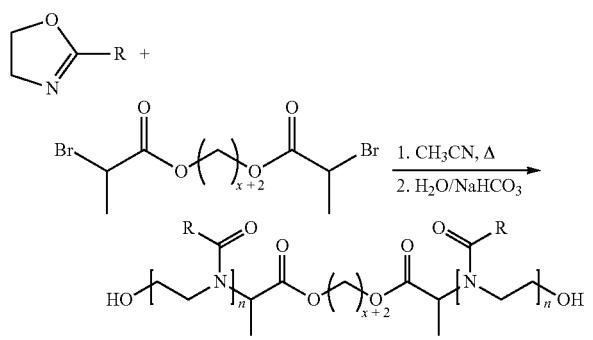

To a flame-dried, 2-necked 250-mL round bottom flask equipped with stopper and stir bar, and a condenser, was added via syringe 2-ethyl-2-oxazoline (25 mL), ethylene glycol bis(2-bromoprionate) (0.568 grams), and acetonitrile (55 mL). The flask was placed in an 80° C. oil bath under $N_{2(g)}$ and allowed to stir overnight. The reaction was terminated by adding sodium bicarbonate (0.12 grams) and deionized (DI) water (0.2 mL) and allowed to stir for one hour. The resulting polymer was precipitated into about 1500 mL diethyl ether, filtered, and dried in a vacuum oven.

Example 2

A polyoxazoline having a number average molecular weight of 5,000 Daltons was prepared according to the following reaction scheme.

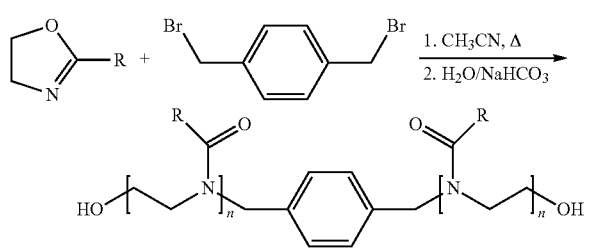

To a flame-dried 2-necked 250-mL round bottom flask equipped with stopper and stir bar, and a condenser was added, via a syringe, 2-ethyl-2-oxazoline (25 mL), α, α'-dibromo-p-xylene (0.45 grams), and acetonitrile (55 mL). The flask was placed in an 80° C. oil bath under $N_{2(g)}$ and allowed to stir overnight. The reaction was terminated by adding sodium bicarbonate (0.12 grams) and DI water (0.2 mL) and allowed to stir for one hour. The resulting polymer was precipitated into about 1500 mL diethyl ether, filtered, and dried in a vacuum oven.

Example 3

A polyoxazoline having a number average molecular weight of 700 Daltons and a weight average molecular weight of 7,700 Daltons was prepared according to the following reaction scheme.

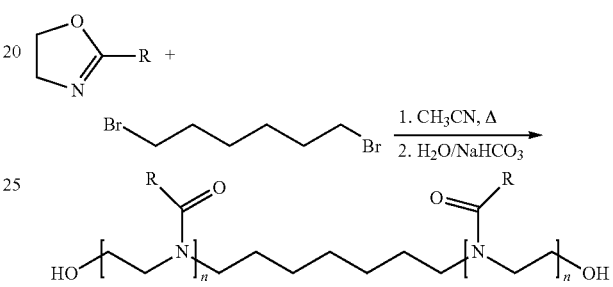

To a flame-dried 2-necked 250-mL round bottom flask equipped with stopper and stir bar, and a condenser was added, via a syringe, 2-ethyl-2-oxazoline (25 mL), 1,6-dibromohexane (0.26 mL), and acetonitrile (55 mL). The flask was placed in an 80° C. oil bath under $N_{2(g)}$ and allowed to stir overnight. The reaction was terminated by adding sodium bicarbonate (0.12 grams) and DI water (0.2 mL) and allowed to stir for one hour. The resulting polymer was precipitated into about 1500 mL diethyl ether, filtered, and dried in a vacuum oven.

Example 4

A polyoxazoline having a number average molecular weight of 800 Daltons and a weight average molecular weight of 14,400 Daltons was prepared according to the following reaction scheme.

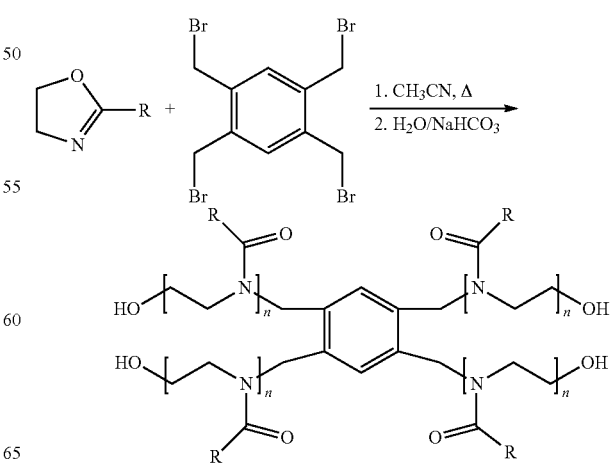

To a flame-dried 2-necked 250-mL round bottom flask equipped with stopper and stir bar, and a condenser was added, via a syringe, 2-ethyl-2-oxazoline (25 mL), 1,2,5,6-tetrakis(bromomethyl) benzene (0.77 grams), and acetonitrile (55 mL). The flask was placed in an 80° C. oil bath under N$_{2(g)}$ and allowed to stir overnight. The reaction was terminated by adding sodium bicarbonate (0.12 grams) and DI water (0.2 mL) and allowed to stir for one hour. The resulting polymer was precipitated into about 1500 mL diethyl ether, filtered, and dried in a vacuum oven.

Example 5

A polyoxazoline having a number average molecular weight of 4,900 Daltons and a weight average molecular weight of 9,135 Daltons was prepared according to the following reaction scheme.

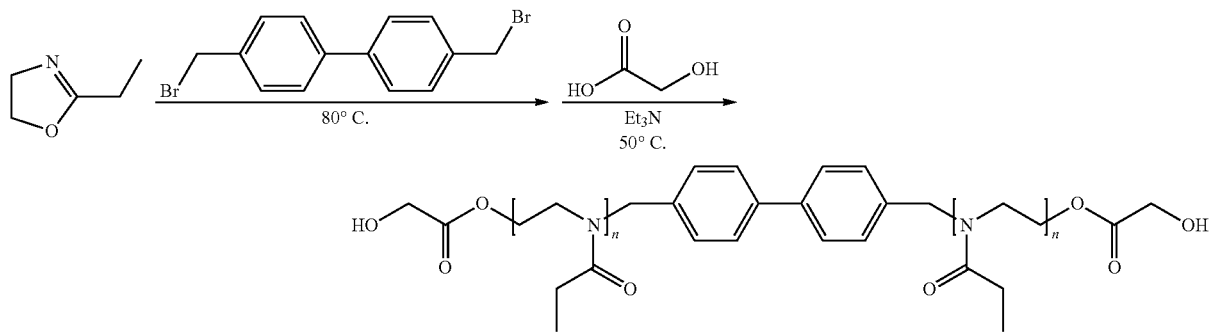

To a flame-dried 2-necked 250-mL round bottom flask was added 4,4'-bis(bromomethyl)biphenyl (0.54 g; 0.0016 mol) and 20 mL of anhydrous acetonitrile. Next, 2-ethyl-2-oxazoline (24.55 g; 0.2476 mol) was added by syringe. The flask was placed in a preheated oil bath at 80° C. for about 6 hours to produce a polymer in ether and then cooled. Glycolic acid (2.20 g; 0.037 mol) and triethylamine (1.24 g; 0.012 mol) were added sequentially and placed in a preheated oil bath at 50° C. overnight. Additional solvent (~5 mL) was added to keep the reaction stirring.

The mixture was cooled, diluted with dichloromethane (400 mL), washed with saturated aqueous sodium bicarbonate (2×300 mL) and saturated aqueous sodium chloride (1×300 mL). The combined bicarbonate extracts were back extracted with 1×400 mL of dichloromethane. The combined organics were dried over magnesium sulfate and evaporated. Next, dichloromethane (about 100 mL) was added to the residue and precipitated into ether. The polymer was collected, dried, redissolved in dichloromethane and precipitated into ether. The solid was filtered, rinsed and dried over a several days in a house vacuum oven at room temperature. A white solid was collected (18.60 g) (76%).

Example 6

Preparation of Polyoxazoline-Based, Silicone-Containing Polyurethane.

To a flame-dried 2-necked 250-mL round bottom flask equipped with stopper, stir bar, additional funnel and a condenser, and under nitrogen to maintain dry environment, was added the polyoxazoline polymer of Example 2 (6.43 grams) with 1,2-dichloroethane (76 mL/100 grams mixture). After the polymer was dissolved, Silsurf® 2510 (45.89 grams), triethylene glycol (13.14 grams), and dibutyl tin dilaurate (0.05 grams) were added. The flask was placed in a heated oil bath (80° C.) and stirred to combine the components. Next, 4,4'-methylene bis (cyclohexyl isocyanate) (34.50 grams) was added via syringe. The reaction mixture was stirred for a minimum of 2 hours under nitrogen while maintaining 80° C. The reaction mixture was then cooled to room temperature and poured onto treated glass plates to make thin film. The solvent was evaporated in the hood overnight.

Various features disclosed herein are, for brevity, described in the context of a single embodiment, but may also be provided separately or in any suitable sub-combination. All combinations of the embodiments are specifically embraced by the illustrative embodiments disclosed herein just as if each and every combination was individually and explicitly disclosed. In addition, all sub-combinations listed in the embodiments describing such variables are also specifically embraced by the present formulations and are disclosed herein just as if each and every such sub-combination was individually and explicitly disclosed herein.

It will be understood that various modifications may be made to the embodiments disclosed herein. Therefore, the above description should not be construed as limiting, but merely as exemplifications of preferred embodiments. For example, the functions described above and implemented as the best mode for operating the embodiments disclosed herein are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A biomedical device which is a polymerization product of a mixture comprising:
   (a) about 20 to about 60 weight percent, based on the total weight of the mixture, of one or more difunctional isocyanates;
   (b) about 10 to about 70 weight percent, based on the total weight of the mixture, of one or more polyalcohols;
   (c) about 10 to about 70 weight percent, based on the total weight of the mixture, of one or more hydroxy-terminated polysiloxane prepolymers; and
   (d) about 5 to about 65 weight percent, based on the total weight of the mixture, of one or more polyoxazoline polyols having a weight average molecular weight of equal to or greater than about 1000 Daltons.

2. The biomedical device of claim 1, wherein the one or more difunctional isocyanates comprise an aliphatic isocyanate, a cycloaliphatic isocyanate and an aromatic isocyanate.

3. The biomedical device of claim 1, wherein the one or more difunctional isocyanates are of the formula OCN—$R^1$—NCO, wherein $R^1$ is a linear or branched $C_3$-$C_{18}$-alkylene group, a $C_6$-$C_{10}$-arylene group, a $C_7$-$C_{18}$-aralkylene group, a $C_6$-$C_{10}$-arylene-$C_1$-$C_2$-alkylene-$C_6$-$C_{10}$-arylene group, a $C_3$-$C_8$-cycloalkylene group, a $C_3$-$C_8$-cycloalkylene-$C_1$-$C_6$-alkylene group, a $C_3$-$C_8$-cycloalkylene-$C_1$-$C_6$-alkylene-$C_3$-$C_8$-cycloalkylene group or a $C_1$-$C_6$-alkylene-$C_3$-$C_8$-cyclo-alkylene-$C_1$-$C_6$-alkylene group.

4. The biomedical device of claim 1, wherein the one or more polyalcohols have from about 2 to about 50 carbon atoms and at least 2 hydroxy groups.

5. The biomedical device of claim 1, wherein the one or more polyalcohols are selected from the group consisting of a diol, a triol, a tertiary amine polyalcohol, an alkoxylated polyalcohol, a polyether polyalcohol, and mixtures thereof.

6. The biomedical device of claim 1, wherein the one or more hydroxy-terminated polysiloxane prepolymers are of the formula:

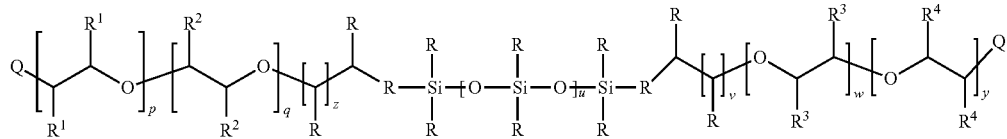

wherein each R, $R^1$, $R^2$, $R^3$ and $R^4$ group independently represents H or a hydrocarbyl group; p is an integer from 0 to 40; q is an integer from 0 to 40; z is an integer from 2 to 50; u is an integer from 1 to 100; y is an integer from 0 to 40; w is an integer from 0 to 40; v is an integer from 2 to 50; and each Q group independently represents a hydroxyl-containing reactive functional end group.

7. The biomedical device of claim 1, wherein the one or more polyoxazoline polyols comprise one or more di-functional, tri-functional and tetra-functional polyoxazoline polyols.

8. The biomedical device of claim 7, wherein the one or more di-functional polyoxazoline polyols are one or more polyoxazoline polyols having two oxazoline-containing hydroxyl groups per molecule.

9. The biomedical device of claim 7, wherein the one or more tri-functional polyoxazoline polyols are one or more polyoxazoline polyols having three oxazoline-containing hydroxyl groups per molecule.

10. The biomedical device of claim 7, wherein the one or more polyoxazoline polyols are one or more tetra-functional polyoxazoline polyols having four oxazoline-containing hydroxyl groups per molecule.

11. The biomedical device of claim 1, wherein the one or more polyoxazoline polyols are of the formula:

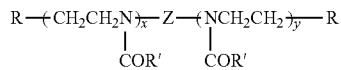

wherein each R is a hydroxyl group; each R' is independently an alkyl group, a haloalkyl group, an alkene group, an alkyne group, a cycloalkyl group, a halocycloalkyl group, an aryl group, a haloaryl group, an aralkyl group and a haloaralkyl group; Z is a divalent linkage and each of x and y are independently at least 1.

12. The biomedical device of claim 1, wherein the mixture further comprises a catalytic amount of one or more catalysts.

13. The biomedical device of claim 1, wherein the mixture comprises:
(a) about 30 to about 45 weight percent, based on the total weight of the mixture, of the one or more difunctional isocyanates;
(b) about 12 to about 20 weight percent, based on the total weight of the mixture, of the one or more polyalcohols;
(c) about 10 to about 50 weight percent, based on the total weight of the mixture, of the one or more hydroxy-terminated polysiloxane prepolymers; and
(d) about 10 to about 45 weight percent, based on the total weight of the mixture, of the one or more polyoxazoline polyols having a weight average molecular weight of equal to or greater than about 1000 Daltons.

14. The biomedical device of claim 1, which is one of a contact lens or an intraocular lens.

15. The biomedical device of claim 1, wherein the polymerization product is a thermosetting polymerization product.

16. A method of making a biomedical device, the method comprising:
(a) providing a mixture comprising:
(i) about 20 to about 60 weight percent, based on the total weight of the mixture, of one or more difunctional isocyanates;
(ii) about 10 to about 70 weight percent, based on the total weight of the mixture, of one or more polyalcohols;
(iii) about 10 to about 70 weight percent, based on the total weight of the mixture, of one or more hydroxy-terminated polysiloxane prepolymers; and
(iv) about 5 to about 65 weight percent, based on the total weight of the mixture, of one or more polyoxazoline polyols having a weight average molecular weight of equal to or greater than about 1000 Daltons;
(b) subjecting the mixture to polymerization conditions to provide a polymerized device; and
(c) hydrating the polymerized device.

17. The method of claim 16, wherein the one or more difunctional isocyanates comprise an aliphatic isocyanate, a cycloaliphatic isocyanate and an aromatic isocyanate, the one or more polyalcohols have from about 2 to about 50 carbon atoms and at least 2 hydroxy groups, and the one or more polyoxazoline polyols are one or more di-functional, tri-functional or tetra-functional polyoxazoline polyols.

18. The method of claim 16, wherein the one or more hydroxy-terminated polysiloxane prepolymers are of the general formula:

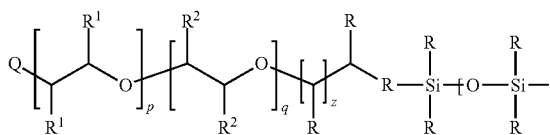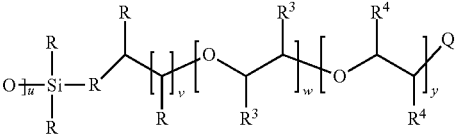

wherein each R, $R^1$, $R^2$, $R^3$ and $R^4$ group independently represents H or a hydrocarbyl group; p is an integer from 0 to 40; q is an integer from 0 to 40; z is an integer from 2 to 50; u is an integer from 1 to 100; y is an integer from 0 to 40; w is an integer from 0 to 40; v is an integer from 2 to 50; and each Q group independently represents a hydroxyl-containing reactive functional end group.

19. The method of claim 16, wherein the one or more polyoxazoline polyols comprise one or more di-functional, tri-functional and tetra-functional polyoxazoline polyols.

20. A biomedical device which is a polymerization product of a mixture comprising:
 (a) one or more difunctional isocyanates;
 (b) one or more polyalcohols;
 (c) one or more hydroxy-terminated polysiloxane prepolymers; and
 (d) one or more polyoxazoline polyols having a weight average molecular weight of equal to or greater than about 1000 Daltons, wherein the one or more polyoxazoline polyols are one or more tetra-functional polyoxazoline polyols having four oxazoline-containing hydroxyl groups per molecule.

21. The biomedical device of claim 20, wherein the mixture comprises:
 (a) about 20 to about 60 weight percent, based on the total weight of the mixture, of the one or more difunctional isocyanates;
 (b) about 10 to about 70 weight percent, based on the total weight of the mixture, of the one or more polyalcohols;
 (c) about 3 to about 60 weight percent, based on the total weight of the mixture, of the one or more hydroxy-terminated polysiloxane prepolymers; and
 (d) about 5 to about 65 weight percent, based on the total weight of the mixture, of the one or more polyoxazoline polyols having a weight average molecular weight of equal to or greater than about 1000 Daltons.

* * * * *